(12) United States Patent
Olson et al.

(10) Patent No.: US 7,996,188 B2
(45) Date of Patent: Aug. 9, 2011

(54) USER INTERFACE FOR A FLOW CYTOMETER SYSTEM

(75) Inventors: David Olson, Ann Arbor, MI (US); Collin A. Rich, Ypsilanti, MI (US); Clement James Goebel, III, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 832 days.

(21) Appl. No.: 11/466,391

(22) Filed: Aug. 22, 2006

(65) Prior Publication Data

US 2008/0228444 A1    Sep. 18, 2008

Related U.S. Application Data

(60) Provisional application No. 60/710,102, filed on Aug. 22, 2005.

(51) Int. Cl.
*G01N 15/00* (2006.01)
*G06F 17/40* (2006.01)

(52) U.S. Cl. .............. 702/189; 702/45; 702/21; 702/32; 422/73

(58) Field of Classification Search ................. 702/189, 702/45, 21, 32
See application file for complete search history.

(56) References Cited

U.S. PATENT DOCUMENTS

| | | | |
|---|---|---|---|
| 4,691,829 A | 9/1987 | Auer | |
| 5,150,313 A | 9/1992 | van den Engh et al. | |
| 5,204,884 A | 4/1993 | Leary et al. | |
| 5,224,058 A * | 6/1993 | Mickaels et al. | ................ 702/19 |
| 5,270,548 A | 12/1993 | Steinkamp | |
| 5,308,990 A | 5/1994 | Takahashi et al. | |
| 5,367,474 A | 11/1994 | Auer | |
| 5,469,375 A | 11/1995 | Kosaka | |
| 5,684,480 A | 11/1997 | Jansson | |
| 5,883,378 A | 3/1999 | Irish | |
| 5,981,180 A | 11/1999 | Chandler | |
| 6,115,065 A | 9/2000 | Yadid-Pecht | |
| 6,181,319 B1 | 1/2001 | Fujita | |
| 6,710,871 B1 | 3/2004 | Goix | |
| 6,778,910 B1 | 8/2004 | Vidal | |
| 6,809,804 B1 | 10/2004 | Yount | |
| 6,816,257 B2 | 11/2004 | Goix | |
| 6,897,954 B2 | 5/2005 | Bishop | |
| 7,019,834 B2 | 3/2006 | Sebok | |
| 7,024,316 B1 | 4/2006 | Ellison | |
| 7,106,442 B2 | 9/2006 | Silcott | |
| 7,130,046 B2 | 10/2006 | Fritz | |
| 7,274,316 B2 | 9/2007 | Moore | |
| 7,362,432 B2 * | 4/2008 | Roth | ............................. 356/317 |

(Continued)

FOREIGN PATENT DOCUMENTS

JP    356169978 A    12/1981

(Continued)

*Primary Examiner* — Hal D Wachsman
(74) *Attorney, Agent, or Firm* — Jeffrey Schox

(57) ABSTRACT

A method of extracting and analyzing a data set from a flow cytometer system of the preferred embodiment comprises the steps of (1) running a sample and saving all collected raw data, (2) viewing raw (or "unmodified") data, (3) modifying the raw data (e.g., scaling and/or culling the raw data), (4) reviewing and saving the modified data, and (5) exporting the saved data. Once the sample has been run and all collected data have been saved, the user can repeat the steps of modifying the raw data, saving the modified data, and exporting the saved data as many times as necessary and/or desirable.

36 Claims, 2 Drawing Sheets

U.S. PATENT DOCUMENTS

| | | |
|---|---|---|
| 2002/0028434 A1 | 3/2002 | Goix et al. |
| 2002/0080341 A1 | 6/2002 | Kosaka |
| 2003/0054558 A1 | 3/2003 | Kurabayashi |
| 2003/0078703 A1* | 4/2003 | Potts et al. ................ 701/1 |
| 2003/0223061 A1 | 12/2003 | Sebok |
| 2004/0131322 A1 | 7/2004 | Ye et al. |
| 2004/0143423 A1* | 7/2004 | Parks et al. ............ 702/194 |
| 2004/0246476 A1 | 12/2004 | Bevis et al. |
| 2005/0073686 A1* | 4/2005 | Roth et al. ............ 356/436 |
| 2006/0015291 A1* | 1/2006 | Parks et al. ............ 702/179 |
| 2006/0219873 A1* | 10/2006 | Martin et al. ............ 250/214 R |
| 2007/0124089 A1* | 5/2007 | Jochum et al. ............ 702/32 |
| 2008/0228444 A1 | 9/2008 | Olson et al. |
| 2010/0012853 A1 | 1/2010 | Parks et al. |

FOREIGN PATENT DOCUMENTS

| | | |
|---|---|---|
| WO | 2005017499 | 2/2005 |
| WO | 2005068971 | 7/2005 |
| WO | 2005091893 | 10/2005 |
| WO | 2010/101623 | 9/2010 |

* cited by examiner

Figure 1 – Prior Art
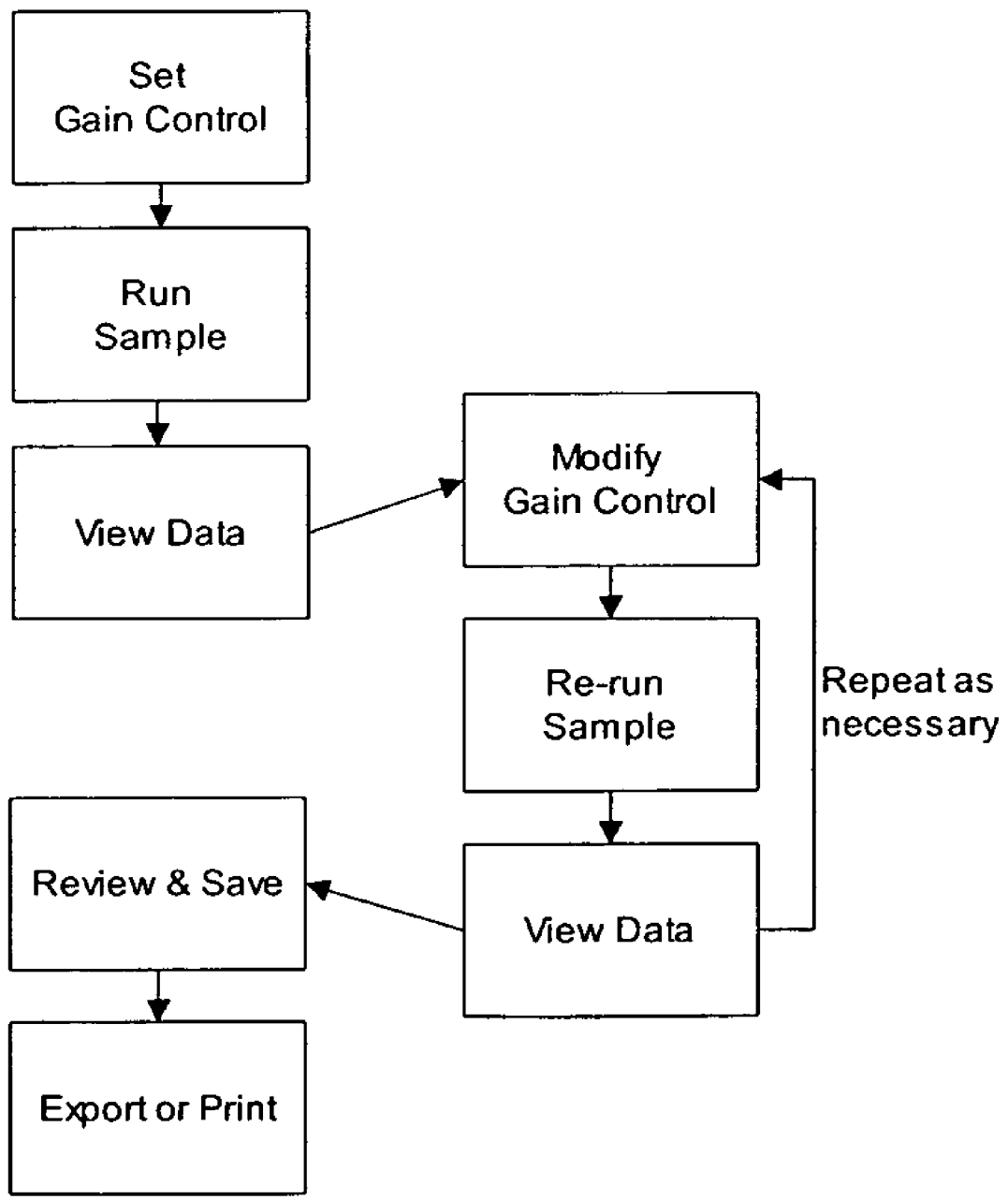

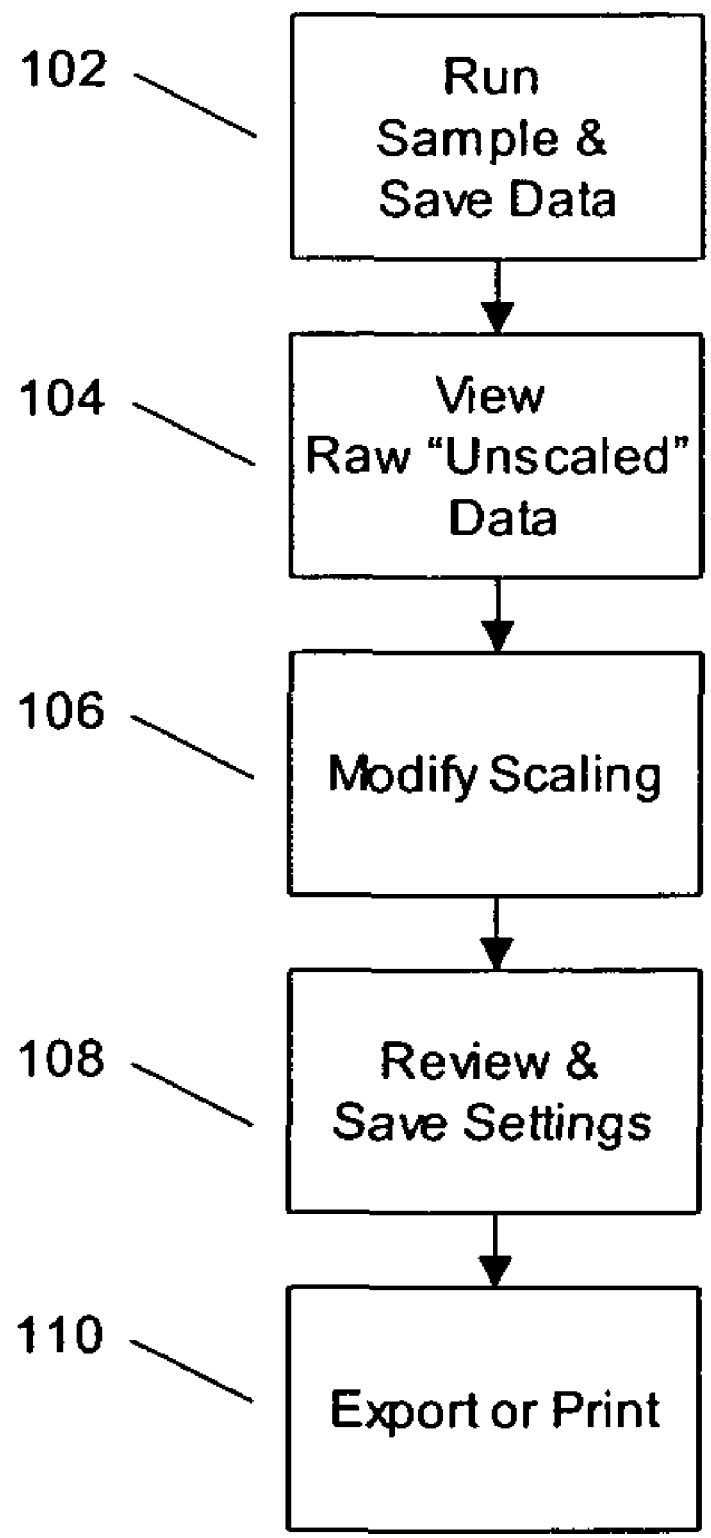

USER INTERFACE FOR A FLOW CYTOMETER SYSTEM

CROSS-REFERENCE TO RELATED APPLICATIONS

This application claims the benefit of U.S. Provisional Application No. 60/710,102, entitled "User Interface for a Flow Cytometer System" and filed on 22 Aug. 2005, which is incorporated in its entirety by this reference.

TECHNICAL FIELD

The present invention relates generally to the field of flow cytometers, and more particularly to user interfaces in the field of flow cytometers.

BACKGROUND

A typical flow cytometer detector has a limited collection range. In quantitative terms, the collection range for a typical flow cytometer with a photomultiplier tube is approximately four decades, whereas the signal range of the objects may span more than five decades across experiments. In simple terms, the collection range of a typical flow cytometer is smaller than the signal range of the objects. For this reason, the typical detector is supplied with a gain level for the photomultiplier tubes and/or an amplifier. Detectors typically collect data relative to an object's size (light scatter) or brightness (fluorescence); both types of data are often collected on each object detected. To collect signals from small or faint objects, the gain level is increased. With an increased gain level, however, the signals from large or bright objects are too intense to be collected. To collect signals from large or bright objects, the gain level is decreased. With a decreased gain level, however, the signals from small or faint objects are too weak to be collected.

As shown in FIG. 1, the typical flow cytometer user interface involves the preparation and running of a pilot sample in order to appropriately set the gain control and define the user-set collection range. This involves the steps of (1) setting the gain control to what the user predicts will provide the desired collection range, (2) running a pilot sample through the flow cytometer, (3) viewing the pilot data/signal collected from the pilot sample, (4) identifying the extent to which, if any, the gain setting should be modified to achieve a more suitable collection range, and (5) repeating steps 1-4 as needed until the desired collection range is achieved. Since the typical detector is unable to obtain useable data from signals beyond its collection range, and since the typical detector requires a pre-set gain level, the typical user interface does not allow the user to adjust the signal gain level/scaling (e.g. photomultiplier tube voltages) after data acquisition is complete. Observing data signals outside of the pre-set collection range is only possible if (1) the user changes the detector gain levels and (2) the user is able to run an additional test sample that is relatively homogenous to the previous samples and is temporally stable.

The limitations of the user interface of typical flow cytometer systems have at least four disadvantages: (1) the expenditure of valuable user time spent on the gain-setting process to ensure it is set correctly; (2) the requirement of significantly more sample to determine the proper gain settings (i.e. more sample is used setting the gain than is actually used in the data collection run), (3) the potential loss of valuable data because the user incorrectly anticipated the actual signal range and a portion or more of the input signals are outside the user-set "active" dynamic collection range and are not collected; and (4) the inability to observe and "undo" changes in user-set gain/scaling settings without running additional samples.

As flow cytometer systems incorporate features that significantly increase the collection ranges to a range that approaches the object signal ranges (e.g. broad dynamic range flow cytometers), there will be a need in the flow cytometer field to create a new and improved flow cytometer user interface that avoids or minimizes one or more of these disadvantages. This invention provides such new and improved flow cytometer user interface.

BRIEF DESCRIPTION OF THE FIGURES

FIG. 1 is a schematic block diagram of a flow cytometer user interface of the prior art.

FIG. 2 is a schematic block diagram of a flow cytometer user interface in accordance with the preferred embodiment of the present invention.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

The preferred embodiment of the invention extracts data from the full dynamic range of a flow cytometer in a single run, and then manipulates scaling and/or culling factors across the full dynamic range after the data have been collected. The data of the full dynamic range are collected and stored in raw or unmodified form during the acquisition step and the user interface can display the unmodified data and/or modified data. Because scaling and/or culling factors can be applied after the acquisition step is complete, the user interface facilitates real-time comparisons between the raw and modified data on a single, unique sample run. Scaling and/or culling can be adjusted or undone without the need to re-run pilot samples, which saves time, reduces the amount of sample required, and eliminates the potential of lost data due to incorrect gain settings.

As shown in FIG. 2, the flow cytometer user interface of the preferred embodiment comprises the steps of (1) running the sample and saving all collected data, (2) viewing the raw (or "unmodified") data, (3) modifying the raw data (e.g., scaling and/or culling the raw data), (4) reviewing and saving the modified settings, and (5) exporting the saved data. Once the sample has been run and all collected data have been saved, the user can repeat the steps of modifying the raw data, saving the modified settings, and exporting the saved data as many times as necessary or desirable without the need to run an additional sample.

The user interface of the preferred embodiment may be coupled to any suitable diagnostic and/or analysis system. In the preferred embodiment, the user interface is in electronic communication with an advanced flow cytometer that has a collection range that approaches the total detected object signal range (e.g. broad dynamic range flow cytometers). While the advanced flow cytometer may be any suitable flow cytometer system, it is preferably an advanced flow cytometer as described in U.S. Patent Publication No. 2006/0219873, entitled "Detection System for a Flow Cytometer" and filed on 31 Mar. 2006, which is incorporated in its entirety by this reference. In an alternative embodiment, the user interface is in electronic communication with a composite of several narrow dynamic range flow cytometers.

In the preferred embodiment, the first step of 'running the sample and saving all collected data' (102) includes the collection (i.e., acquisition) and electronic storage of the full dynamic range of input signals (in raw, unmodified format) from a flow cytometer sample. The full dynamic range of input signals is preferably defined as the range of input signals that provides a 1:100,000 ratio, and more preferably a 1:1,000,000 ratio, between the faintest objects and the brightest objects. The full dynamic range of input signals is preferably captured by a 24bit process, which translates to roughly 16,700,000 levels of information, but may alternatively be captured by any suitable process. Preferably, the captured data includes an error rate induced by electric noise of less than one-percent. In the preferred embodiment, the data are collected in a raw, unmodified format without the use of, or the adjustment in, the gain level of the detector. The collection of the data in this manner eliminates the expenditure of valuable user time and avoids the potential loss of valuable data through misconfiguration of the system.

The second step of 'viewing the raw data' (104) permits the user to observe the raw data that has been collected and stored from the sample run and identify the anticipated appropriate modifications for the sample. In the preferred embodiment, the user interface presents the raw data after the acquisition is complete. In an alternative embodiment, the user interface presents the raw data during the acquisition step. In a first "local" variation of the preferred embodiment, the original, raw data set to be viewed is acquired from a flow cytometer coupled to the user interface; in a second "remote" variation, the original data set is acquired from an electronic storage medium. When the user interface is coupled to a broad dynamic range flow cytometer, as in the preferred embodiment, the user interface can display data from greater than four decades of signal.

The third step of 'modifying the raw data' (106) permits the user to manipulate (e.g. scale and/or cull) the data collected across the full dynamic range of input signals from the flow cytometer sample. In this step, the user interface permits the user to perform real-time comparisons between the raw and modified data on a single, unique sample run. Additionally, scaling and/or culling can be adjusted or undone without the need to re-run pilot samples allowing multiple adjustments on the same initial data set.

In the preferred embodiment, the user scales and/or culls the raw data to select a subset of signals that corresponds to the desired sample population. The user is permitted to apply gain and scaling factors to the acquired data. This is performed independently of the acquisition step and permits the user to adjust the bounds of the data. In an alternative embodiment, the user interface automatically scales and/or culls the raw data based on an appropriate algorithm. In this alternative embodiment, the user interface may accept a user command that corresponds to, or identifies, the desired sample population. The modifying of raw data preferably occurs after data acquisition is complete, and multiple signal gain/scaling adjustments can be made on a single, unique data set.

The user interface of the preferred embodiment may be virtual, physical, or any suitable combination. In the virtual variation, the knobs, sliders, and other controls are shown only on a display and not in a physical unit. The controls, whether virtual or physical, permit the single, unique data set to be modified in a step-wise, sequential fashion. Alternatively, the user interface may permit the single, unique data to be repeatedly or iteratively modified. Scaling is preferably applied hierarchically based on forward scatter, which can be expanded to include any or all of the available data channels (scatter and fluorescent) in a progressive fashion. Scaling may, however, be applied in any suitable manner.

Any number of subsets of data can be generated that correspond to one or more sample populations contained within the raw data set. Preferably, the user interface permits each subset (i.e. modification) of the raw data and the settings used to generate the desired subset of data to be individually saved, recorded, and identified. Alternatively, the user interface may permit subsets of raw data that are generated by sequential or iterative modifications and the settings used to generate the desired subset of data to be saved and identified at each iteration and in their totality.

In the preferred embodiment, the user interface utilizes one or more graphical, menu-driven formats that can accept and display data sets, such as those from a flow cytometer with broad dynamic range. In an alternative embodiment, the user interface utilizes a numerical display format. The user interface permits the application of scaling and/or culling factors to the original data set to modify its display representation. In a first variation, the user interface simultaneously presents modified and raw representations of a single data set. In a second variation, the user interface simultaneously presents multiple data sets that can be simultaneously viewed, compared, and analyzed. The user can undo or otherwise alter the modifications of one or more data sets using the menu-driven options.

The user interface of the preferred embodiment represents raw data and modified data using any suitable format, including graphically and numerically. The user interface enables observation of the consequences of scaling and/or culling modifications on a unique data set by simultaneous representation of raw and modified data. In one variation, separate graphs are generated from the raw and modified data and are displayed in separate frames, which preferably represents a preview of the export/print version of the viewed data. In an alternative variation, the raw and modified data are superimposed on one another in the same graph frame, with each data set preferably distinguished by color and/or shading. In yet another variation, the consequences of each modification applied to the raw data in the generation of the modified data are represented in independent planes of the same graph frame, and all modifications can be superimposed.

The fourth step of 'reviewing and saving the modified settings' (108) permits the user to identify the modifications made to the original data set and to store the setting(s) used to generate the desired subset of data, thus allowing the user to save both the data and the corresponding scaling and/or culling parameters. The user interface provides virtual instrument settings that can be adjusted, which generate a corresponding subset of data from the raw (i.e. original) data set. The user can repeat the steps of modifying the raw data and saving the desired subset of data and modified settings as many times as necessary and/or desirable, without the need for running additional sample through the flow cytometer. If the user generates the subset of data by making one or more alterations in the virtual settings, the user can access the previously saved alterations made to the subset of data and retrace or "undo" the alterations sequentially. In the preferred embodiment, the user interface will prompt the user to save the modified subset of data, the settings used to generate the data, and any other pertinent information regarding the sample or data acquisition; in an alternative embodiment, the data settings are saved automatically. The user interface can apply hierarchical scaling factors to independent data channels (e.g. scatter channels and fluorescent channels).

The fifth step of 'exporting the saved data' (110) permits the user to transfer the original (raw) data set and/or the modified subset of data from the flow cytometer system to a different medium, such as a printout or an electronic file. The data may be transferred to any suitable medium for subsequent viewing, analysis, and/or storage, and the settings used to generate the data and other pertinent information regarding the sample or data acquisition may also be included.

As a person skilled in the art of flow cytometry will recognize from the previous detailed description and from the figures and claims, modifications and changes can be made to the preferred embodiment of the invention without departing from the scope of this invention defined in the following claims.

We claim:

1. A method of extracting and analyzing a data set from a flow cytometer system comprising:
   collecting a full dynamic range of input signals from a flow cytometer sample;
   storing an initial data set of the full dynamic range of the input signals from the flow cytometer sample;
   displaying the initial data set on a user interface;
   allowing modification of the initial data set to manipulate the initial data set across the range of input signals from the flow cytometer sample;
   saving the modified data set; and
   exporting the saved data set to a different medium than the flow cytometer system;
   wherein collecting the full dynamic range of input signals includes collecting the full dynamic range of input signals to an initial data set that includes a 1:100,000 ratio between the faintest objects and the brightest objects.

2. The method of claim 1 wherein collecting the full dynamic range of input signals further includes collecting the full dynamic range of input signals to an initial data set with an error rate induced by electric noise of less than one-percent.

3. The method of claim 1 wherein collecting the full dynamic range of input signals further includes collecting the input signals without accepting a gain amplification level selection from a user.

4. The method of claim 1 wherein storing an initial data set includes storing to an electronic storage unit.

5. The method of claim 1 wherein displaying the initial data set includes permitting a user to observe the initial data set from the full dynamic range of input signals, and permitting the user to identify the appropriate modifications for the initial data set.

6. The method of claim 1 wherein exporting the saved data set includes permitting a user to transfer at least one of the initial data set and the modified data set from the flow cytometer method to the different medium.

7. The method of claim 1 wherein allowing modification of the initial data set includes permitting a user to manipulate the initial data set across the full dynamic range of input signals from the flow cytometer sample and to generate a modified data set.

8. The method of claim 7 wherein allowing modification of the initial data set further includes permitting the user to:
   perform real-time comparisons between the initial data set and the modified data set on a single flow cytometer sample,
   adjust or undo modifications, to make multiple adjustments on the same initial data set, and
   generate at least one subset of data that corresponds to one or more sample populations contained within the initial data set.

9. The method of claim 1 wherein allowing modification of the initial data set further includes permitting a user to identify the modifications made to the initial data set and to store settings used to generate a desired subset of data.

10. The method of claim 9 wherein allowing modification of the initial data set further includes providing adjustable virtual instrument settings.

11. The method of claim 9 wherein allowing modification of the initial data set further includes applying hierarchical scaling factors to independent data channels.

12. The method of claim 9 wherein allowing modification of the initial data set further includes utilizing a graphical, menu-driven format adapted to accept and display data sets.

13. A method of extracting and analyzing a data set from a flow cytometer system comprising:
   collecting a full dynamic range of input signals from a flow cytometer sample;
   storing an initial data set of the full dynamic range of the input signals from the flow cytometer sample;
   displaying the initial data set on a user interface;
   allowing modification of the initial data set to manipulate the initial data set across the range of input signals from the flow cytometer sample;
   saving the modified data set; and
   exporting the saved data set to a different medium than the flow cytometer system;
   wherein allowing modification of the initial data set includes permitting a user to manipulate the initial data set across the full dynamic range of input signals from the flow cytometer sample and to generate a modified data set, wherein allowing modification of the initial data set further includes permitting the user to:
   perform real-time comparisons between the initial data set and the modified data set on a single flow cytometer sample,
   adjust or undo modifications, to make multiple adjustments on the same initial data set, and
   generate at least one subset of data that corresponds to one or more sample populations contained within the initial data set.

14. The method of claim 13 wherein allowing modification of the initial data set further includes permitting the user to adjust the bounds of the data.

15. The method of claim 13 wherein collecting the full dynamic range of input signals includes collecting the full dynamic range of input signals to an initial data set that includes a 1:100,000 ratio between the faintest objects and the brightest objects.

16. The method of claim 15 wherein collecting the full dynamic range of input signals further includes collecting the full dynamic range of input signals to an initial data set with an error rate induced by electric noise of less than one-percent.

17. The method of claim 13 wherein collecting the full dynamic range input signals further includes collecting the input signals without accepting a gain amplification level selection from a user.

18. The method of claim 13 wherein displaying the initial data set includes permitting a user to observe the initial data set from the full dynamic range of input signals, and permitting the user to identify the appropriate modifications for the initial data set.

19. The method of claim 18 wherein allowing modification of the initial data set further includes permitting a user to identify the modifications made to the initial data set and to store settings used to generate a desired subset of data.

20. The method of claim 19 wherein allowing modification of the initial data set further includes providing adjustable virtual instrument settings.

21. The method of claim 19 wherein allowing modification of the initial data set further includes applying hierarchical scaling factors to independent data channels.

22. The method of claim 13 wherein allowing modification of the initial data set further includes utilizing a graphical, menu-driven format adapted to accept and display data sets.

23. A method of extracting and analyzing a data set from a flow cytometer system comprising:
    collecting a full dynamic range of input signals from a flow cytometer sample;
    storing an initial data set of the full dynamic range of the input signals from the flow cytometer sample;
    displaying the initial data set on a user interface;
    allowing modification of the initial data set to manipulate the initial data set across the range of input signals from the flow cytometer sample;
    saving the modified data set; and
    exporting the saved data set to a different medium than the flow cytometer system;
wherein allowing modification of the initial data set further includes permitting a user to identify the modifications made to the initial data set and to store settings used to generate a desired subset of data.

24. The method of claim 23 wherein allowing modification of the initial data set further includes providing adjustable virtual instrument settings.

25. The method of claim 23 wherein allowing modifications of the initial data set further includes applying hierarchical scaling factors to independent data channels.

26. The method of claim 23 wherein allowing modification of the initial data set further includes utilizing a graphical, menu-driven format adapted to accept and display data sets.

27. The method of claim 26 wherein utilizing a graphical, menu-driven format includes displaying separate graphs that are generated from the initial data set and the modified data set in separate frames.

28. The method of claim 26 wherein utilizing a graphical, menu-driven format includes superimposing the initial data set and the modified data set on one another and displaying them in the same graph frame, distinguishing each data set.

29. The method of claim 26 wherein utilizing a graphical, menu-driven format includes displaying, in independent planes of the same graph frame, the consequences of each modification applied to the initial data set in the generation of the modified data set.

30. The method of claim 23 wherein allowing modification of the initial data set further includes utilizing a numerical display format.

31. The method of claim 23 wherein saving the modified data set further includes permitting the user to sequentially access the previously saved alterations made to the subset of data in the settings.

32. The method of claim 23 wherein saving the modified data set further includes saving the corresponding modification parameters and saving other pertinent information regarding the sample or data acquisition.

33. The method of claim 23 wherein collecting the full dynamic range of input signals includes collecting the full dynamic range of input signals to an initial data set that includes a 1:100,000 ratio between the faintest objects and the brightest objects.

34. The method of claim 23 wherein collecting the full dynamic range of input signals further includes collecting the full dynamic range of input signals to an initial data set with an error rate induced by electric noise of less than one-percent.

35. The method of claim 23 wherein collecting the full dynamic range input signals further includes collecting the input signals without accepting a gain amplification level selection from a user.

36. The method of claim 35 wherein displaying the initial data set includes permitting a user to observe the initial data set from the full dynamic range of input signals, and permitting the user to identify the appropriate modifications for the initial data set.

* * * * *

UNITED STATES PATENT AND TRADEMARK OFFICE
CERTIFICATE OF CORRECTION

PATENT NO. : 7,996,188 B2
APPLICATION NO. : 11/466391
DATED : August 9, 2011
INVENTOR(S) : David Olson et al.

It is certified that error appears in the above-identified patent and that said Letters Patent is hereby corrected as shown below:

In Claim 17, line 2, "dynamic range input signals" should read --dynamic range of input signals--
In Claim 35, line 2, "dynamic range input signals" should read --dynamic range of input signals--

Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,996,188 B2 | Page 1 of 1 |
| APPLICATION NO. | : 11/466391 | |
| DATED | : August 9, 2011 | |
| INVENTOR(S) | : David Olson et al. | |

It is certified that error appears in the above-identified patent and that said Letters Patent is hereby corrected as shown below:

Column 6, line 56 (Claim 17, line 2) "dynamic range input signals" should read --dynamic range of input signals--

Column 8, line 32 (Claim 35, line 2) "dynamic range input signals" should read --dynamic range of input signals--

This certificate supersedes the Certificate of Correction issued September 27, 2011.

Signed and Sealed this
Twenty-fifth Day of October, 2011

David J. Kappos
*Director of the United States Patent and Trademark Office*